United States Patent
Todd

(10) Patent No.: US 6,527,792 B1
(45) Date of Patent: Mar. 4, 2003

(54) FOOT AND ANKLE REFLEXOLOGY BANDS

(76) Inventor: Tod M. Todd, 6701 Shady Grove Ct., Citrus Heights, CA (US) 95610

( * ) Notice: Subject to any disclaimer, the term of this patent is extended or adjusted under 35 U.S.C. 154(b) by 156 days.

(21) Appl. No.: 09/656,322

(22) Filed: Sep. 6, 2000

Related U.S. Application Data

(60) Provisional application No. 60/152,782, filed on Sep. 7, 1999.

(51) Int. Cl.[7] .................................................. A61B 17/00
(52) U.S. Cl. .......................................................... 606/204
(58) Field of Search .................................. 606/204, 201; 2/22, 24, 44, 240, 911; 128/171

(56) References Cited

U.S. PATENT DOCUMENTS

| 4,479,495 A | | 10/1984 | Isaacson |
| 4,590,939 A | * | 5/1986 | Sakowski |
| 4,944,289 A | | 7/1990 | Matthews |
| 5,290,307 A | | 3/1994 | Choy |
| 5,584,854 A | * | 12/1996 | Minarik |
| 5,667,484 A | * | 9/1997 | Brossard |
| 5,695,520 A | * | 12/1997 | Bruckner et al. |
| 5,902,259 A | * | 5/1999 | Wilkerson |
| 5,950,239 A | * | 9/1999 | Lopez |

* cited by examiner

Primary Examiner—Ismael Izaguirre
(74) Attorney, Agent, or Firm—Sheldon H. Parker

(57) ABSTRACT

The disclosed invention discloses a flexible band extending around the top of the foot, back of the heel and under the foot proximate the heel. Pressure devices are incorporated at strategic locations to apply pressure to specific areas in accordance with reflexology. An additional strap can be incorporated that either extends around the toe or completely under the foot. Additional pressure devices can be added that correspond to additional reflexology points.

22 Claims, 3 Drawing Sheets

FOOT AND ANKLE REFLEXOLOGY BANDS

This application claims the benefit of Provisional application No. 60/152,782, filed Sep. 7, 1999.

BACKGROUND OF THE INVENTION

1. Field of the Invention

The invention relates a specifically designed and dimensioned foot and ankle band that applies the pressure required for effective reflexology and can be worn for extended time periods.

2. Brief Description of the Prior Art

Reflexology is a healing art that takes advantage of the nerve endings in the hands, ears and feet for relaxation and to improve health. The feet are most commonly used in reflexology as reflex zones in the feet correspond to various parts of the body, including major organs and glands. The body is divided into ten energy zones that correspond to different areas of the feet. In addition to the energy zones, there are nerves stemming from all areas of the body that terminate at the feet. By massaging certain areas on the feet, it is possible to bring a response in the corresponding tissue of the body.

It is also an accepted principle in reflexology that an accumulation of toxins in the feet, primarily acids and calcium, can crystallize around the nerve endings. This crystallization impairs the function of these nerve endings, therefore impairs the function of the correlating organ/gland/tissue. By massaging the various points on the feet, the crystallized deposits can be removed, restoring normal nerve function. This will ultimately restore health to the correlating organ/gland/tissue. Stimulating an area that does not necessarily have crystallized deposits can also stimulate a natural healing/balancing response in the correlating region of the body.

Reflexology and acupressure/acupuncture are not interchangeable and are based upon different body energy. While as reflexology stimulates the nerve ends and specific zones that correspond to areas of the body, acupressure/acupuncture relies on meridians, or energy pathways, within the body.

Acupressure has been addressed in the prior art in such patents as U.S. Pat. No. 5,290,307, which discloses an acupressure belt for the treatment of lower back pain. The belt has multiple acupressure-applying protrusions that, in combination with an adjustable belt, press the protrusions into the back. Another acupressure device is U.S. Pat. No. 4,479,495 that provides a band with an attached stimulator. The '495 device is placed around the leg, arm, etc with the stimulator in the desired position. In U.S. Pat. No. 4,944,289 the acupressure device is used for relieving headaches, applying pressure to the user's head at various points.

In reflexology, consistent pressure over a specified period of time can be necessary to continuously promote the healing process. Manual application, either by the affected person or a practitioner, is generally impossible to implement for any extended period of time. It would also be virtually impossible to manually stimulate many of these points and continue moving about in a productive manner.

The foregoing prior, however, are directed to acupressure points rather than reflex zones. To date, however, no one has addressed the issue of maintaining pressure on reflex zones in accordance with reflexology teachings.

SUMMARY OF THE INVENTION

The disclosed flexible reflexology foot harness delivers, and maintains, pressure to predetermined reflexology points on a user's foot and ankle. The foot harness consists of a front band, a rear band and a heel band, with the length of the straps determining the placement of the pressure points on a user. A first end of each the front band, rear band and heel band are affixed to one another form a first juncture. The first juncture can be formed by permanently or removably affixing the bands to one another. In one embodiment, the second end of the rear band and heel band are permanently affixed to one another, forming a second juncture, with the front band being removably affixed. The front band is preferably affixed to the second juncture using a two part securing method that is adjustable. Alternatively the front, rear and heel band can be manufactured as a single piece. At least one pressure device is affixed to the band in a position to place the device in contact with the center of the appropriate pressure point.

Pressure devices can be placed at each of the junctures and can be stitched or otherwise secured to the material. The pressure devices are polygons, generally circular or semi-circular.

In still another embodiment, the foot harness can use a Y-shaped, securing insert, with affixing means at each end, that is dimensioned to receive the front, rear and heel bands to form second juncture. Using the Y-shaped insert provides additional adjustability. In this embodiment, the second pressure device is affixed to the center of the Y-shaped insert.

In an alternate embodiment, the foot harness can have a toe strap with one end affixed to the front band and the other end with a loop to slide over the user's toe. Alternatively, an anchor strap can be added to the foot harness. The anchor strap has one end secured to the front band and a second end secured to the heel band.

To use the foot harness to apply consistent pressure to the applicable reflexology points, the applicable pressure points are located. The appropriate foot harness size is then determined based on the size of the user's foot. The band is placed on the user's foot with the heel band positioned under the user's foot and the rear band above the user's heel. The pressure devices are positioned adjacent the center of the pressure points and the front band is secured to the second juncture. Consistent, continued pressure is thusly applied to the pressure points.

BRIEF DESCRIPTION OF THE DRAWINGS

The advantages of the instant disclosure will become more apparent when read with the specification and the drawings, wherein.

DETAILED DESCRIPTION OF THE INVENTION

Figure 1:
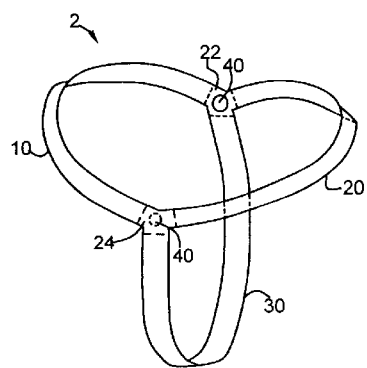
FIG. 1 is a side elevational view of the harness presenting an exterior view of the left side and a partial interior view of the right side contacting the skin of the wearer.

This invention relates to reflexology, an ancient form of healing used by both Egyptian and Chinese cultures. This technique did not become known in the West until the early $20^{th}$-century where it is now being acknowledged as a healing and relaxation technique based on the principles of zone therapy. Typical reflexology therapy generally lasts for 30 to 60 minutes. This time period, although sufficient to enable some relief, may not provide the extended stimulation time necessary. Therefore, for some applications for specific ailments, ten (10) or more sessions can be required.

Acupressure, acupuncture, and reflexology are not the same techniques and do not work on the same principles. Acupressure and acupuncture are both based on meridians, or channels that connect specific areas under the skin to the various organs. Acupressure points are located throughout the body with several points corresponding to each organ. Reflexology addresses issues only through pressure applied to reflex zones on the foot/ankle, hands, and ears. This pressure increases the circulation to these areas as well as increases the nerve supply, stimulating the natural healing process. The increased circulation is partially due to the relaxation that occurs during reflexology and partially due to the stimulation of the pressure zones.

It is an accepted principle in reflexology that an accumulation of toxins in the feet, primarily acids, such as uric, and calcium, can crystallize around the nerve endings, impairing not only their function but also that of the correlating organ/gland/tissue. These crystal deposits, due to gravity, tend to settle more heavily in the feet. The pressure of reflexology breaks up and removes these deposits, restoring normal nerve function. This will ultimately restore health to the correlating organ/gland/tissue. Stimulating an area that does not necessarily have crystallized deposits will also stimulate a natural healing/balancing response in the correlating region of the body.

Specific points on the heels and ankles of both men and women correspond to the reproductive organs, and the manual application of pressure to these points can stimulate a response in the reproductive organs. For a woman, this manual pressure during menses can stimulate the ovaries and relax the uterus. This can help to control and even eliminate menstrual cramps, irregular menstrual cycles, and a variety of other symptoms associated with menses and menopause. The stimulation of the reproductive organs can help normalize the natural production of hormones, ovulation, and menopause. In men, the effect is similar; the prostate and testicles are affected. Stimulation of these organs through the reflexology points can result in normal function being restored. Symptoms such as impotence, premature ejaculation, and enlargement of the prostate can be reduced or completely reversed.

The ankle and foot harness enables continuous stimulation to reflexology points while permitting the user to move about freely. The foot/ankle harness provides consistent pressure to the reflexology points correlating to the reproductive organs for the relief of symptoms and ailments associated with these organs. The harness can be manufactured either to permit adjustability or in various sizes, to accommodate person-to-person variations in the location of the reflexology points. The harness enables the appropriate pressure to be placed simultaneously against the appropriate reflexology points to allow pressure to be maintained over an extended period of time without the hindrance of immobilization. The reflexology points disclosed are associated with the reproductive organs. However other organs can be affected by changing the location of the pressure devices. When moved slightly, the lymph nodes in the groin and armpit, hip, and the sacroiliac joint are affected. Moving the pressure devices to various positions on the current band configuration, i.e. the bottom or rear band, the bladder, low back, fallopian tubes, breasts, knees, cervix, appendix, illeocecal valve, colon, sciatic nerve, small intestines, pelvic region, and rectum are affected. The reflexology points are known and proven effective, it is a convenient method of maintaining of the appropriate pressure at the reflex zone for extended periods of time that that heretofore been unknown.

Figure 3:
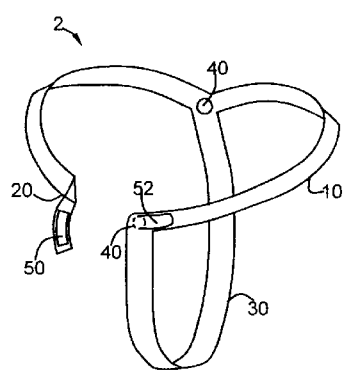
FIG. 3 is a side elevational view of the harness invention with the front band open.
Figure 2:
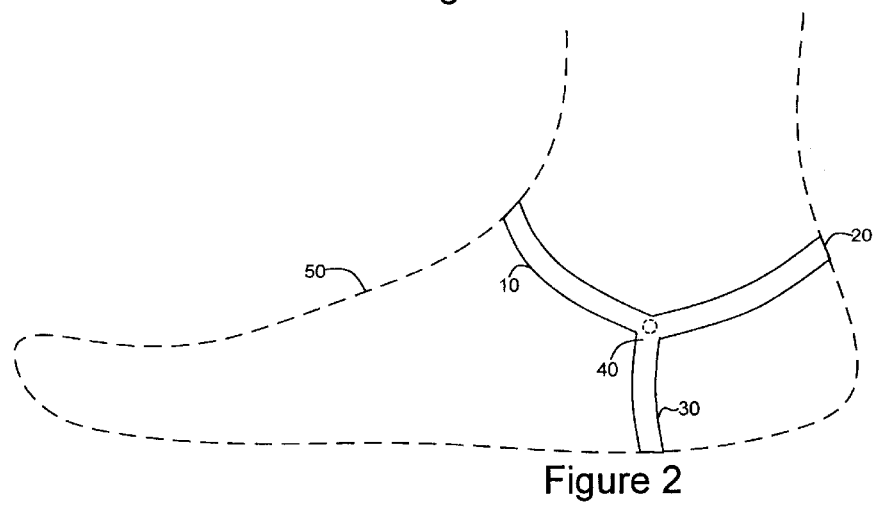
FIG. 2 is a side view of the harness worn by a user.

As seen in FIGS. 1 and 3, the reflexology foot/ankle harness 2 is comprised of three bands, front 10, rear 20, and heel 30, joined at medial junction 22 and lateral junction 24. The medial and lateral junctions 22 and 24 are shown in phantom in FIG. 1 to illustrate the positioning. The bands 10, 20, and 30, in the illustrated embodiments, can be manufactured from one or multiple piece of material. Preferably the material is a conventional fabric material having a relatively small amount of resiliency or stretch. A medial-grade Velstretch is an example of a material that can be used to provide an appropriate measure of thickness and comfort. Depending upon end use, it may be advantageous to have only one or two of the bands manufactured from a stretch material with the remaining band(s) manufactured from a flexible, non-stretchable material.

A closure device, such as the Velcro® fastener 50 and 52 illustrated in FIG. 3, is provided to enable the user to easily put on and remove the device. Other closure devices, such as snaps, singularly or in a series to permit adjustability, buckles, etc. can also be used, and will be obvious to those skilled in the art. For ease of description herein reference will be to Velcro® fasteners, however this is not intended to limit the scope of the invention. In FIG. 3, the hook portion 50 of the Velcro® is placed on the front band 20 while the wool 52 is on the back band 10, preventing the hook portion 50 from becoming caught on the user's clothing. The use of a closure device permits the material used for the bands 10, 20, and 30 to have less flexibility and therefore more adjustability than would be obtained if the harness were slipped over the user's foot. The use of Velcro® provides an easy adjustability, however other methods known in the art, to adjust the length of the front band can be used. Although in the preferred embodiment the harness has some flexibility for comfort purposes, too much elasticity inhibits in effectiveness by permitting the pressure devices to move from the pressure point center as well as not applying the appropriate pressure.

The band 10, 20, and 30 of the harness 2 must be dimensioned to place the pressure devices 40 at the appropriate pressure zones. In the preferred embodiments, the pressure devices 40 have a diameter of about ¼ inch to ½ inch. The plurality of pressure devices 40, such as pearl beads, is positioned at the band junctures 22 and 24 in a manner to apply simultaneous pressure against the reflexology points. It should be noted that the pressure applied by the disclosed device is the pressure exerted in reflexology and not the same pressure applied by acupuncturists or acupressurists. The difference between the types of pressures are well know in the field and will be evident to those skilled in the art. When the disclosed harness is used in conjunction with magnets, or other devices not requiring the same amount of pressure, the harness can be loosened and readjusted, as will be evident to those skilled in the art.

The pressure points illustrated herein correlate to the reproductive organs, however other pressure points can be stimulated by altering the dimensioning of the harness, thereby altering the placement of the beads. The pressure devices 40 are preferably placed within the bands 10, 20, and 30 to reduce manufacturing costs. This, however, is only applicable if the bands 10, 20, and 30 are manufactured from hollow tubing. When the bands are manufactured from a single layer of material, the pressure devices 40 can be maintained in place through the addition of a piece of covering material or stitched into the seam joining the three bands 10, 20 and 30. Alternatively, beads having a center hole enable the pressure devices to be stitching directly onto the material. Other methods, appropriate to the materials being used, will be obvious to those skilled in the art.

The medial zone correlates to the uterus on women and prostate on men. These pressure zones are located at the central flexor retinaculum band between the medial maleolus and the medial surface of the calcaneus. The lateral pressure point correlates to the ovaries on women and testes on men. Pressure is applied to the central peroneal retinaculum running from the lateral maleolus/peroneal trochlea to the lateral surface of the calcaneus. The surface area of this zone is about ¼" by ¼" or 1/16 of a square inch. Other reflex points are larger, such as the bladder and colon regions. To achieve maximum stimulation, and therefore maximum relief, the pressure device 40 must be in the center of the reflex zone. The further from the center of the reflex zone, the less effective the effects. To achieve consistent, accurate placement, the user is fitted with an appropriately sized band with the pressure devices already stitched into place. The use of the various sizes in the band enables the pressure devices to always target the same points. It is further preferable that detailed pictures accompany the band to help the person locate the specific points and make small adjustments to the band in order to align the pressure devices. The sensitivity of the reflex points is also used as an indicator of location. Although bands with adjustable straps can be used, misalignment of the pressure devices can result unless the user is versed in the specific placement. Alternatively, the pressure devices can be adjustable through attachment to Velcro® or a similar method. This will also require heavy education of the purchaser about correct placement.

The reflex zones lie in the same spot, have relatively the same size and require about the same amount of stimulation/pressure in all people, therefore eliminating the need for an increase or decrease in the size of the pressure devices. As the surface area provides little tolerance for variation, the device that will be used by a small woman will not place the pressure devices 40 in an effective position for a large male. This is preferably resolved by manufacturing multiple sizes or an adjustable harness.

Figure 5:
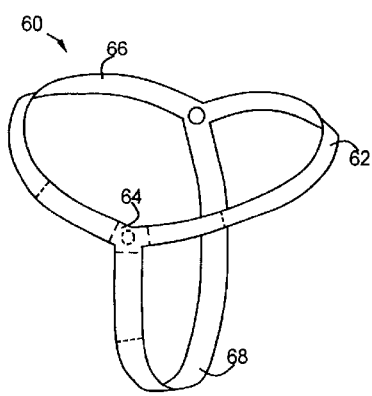
FIG. 5 is a side elevational view of an alternate embodiment incorporating a Y-shaped band in combination with Velcro®.
Figure 6:
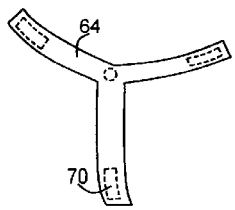
FIG. 6 is a side view of the Y-shaped band and attached Velcro®.
Figure 4:
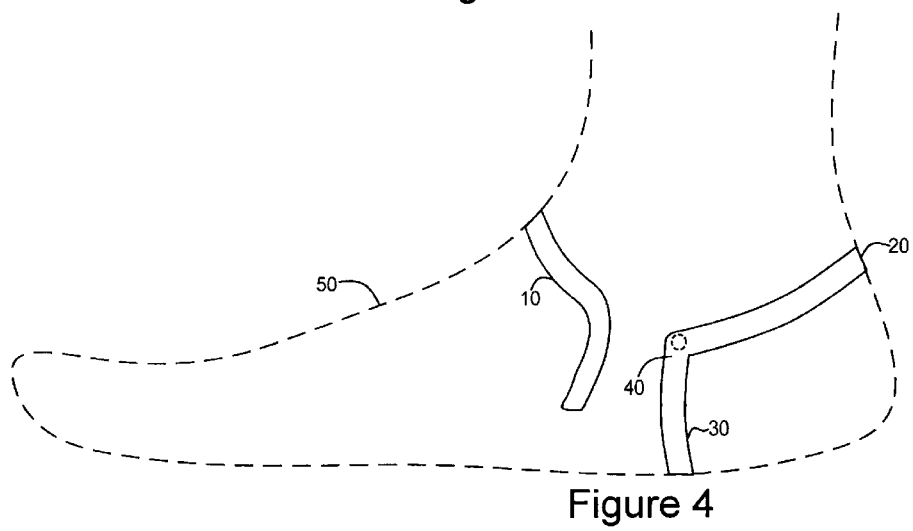
FIG. 4 is a side elevation of the disclosed harness on the user's foot prior to affixing the closure structure.

The harness 60, illustrated in FIGS. 5 and 6, is manufacturing to be adjustable by using a Y-connection 64 having a strip of Velcro® affixed at each of the three ends.

The main structure consists of back band 62, foot band 68 and front band 66, all of which are provided with the opposing Velcro® structure (not shown). The Velcro®, or other adjustable fastening means, enables all three bands of the device to be tightened or loosened as needed for appropriate placement of the pressure devices as taught heretofore. The width of the bands and the exact placement of the pressure devices will vary depending upon the size of the foot and the organs being affected and the exact placement of the pressure devices will be known to those skilled in the art of reflexology.

Figure 7:
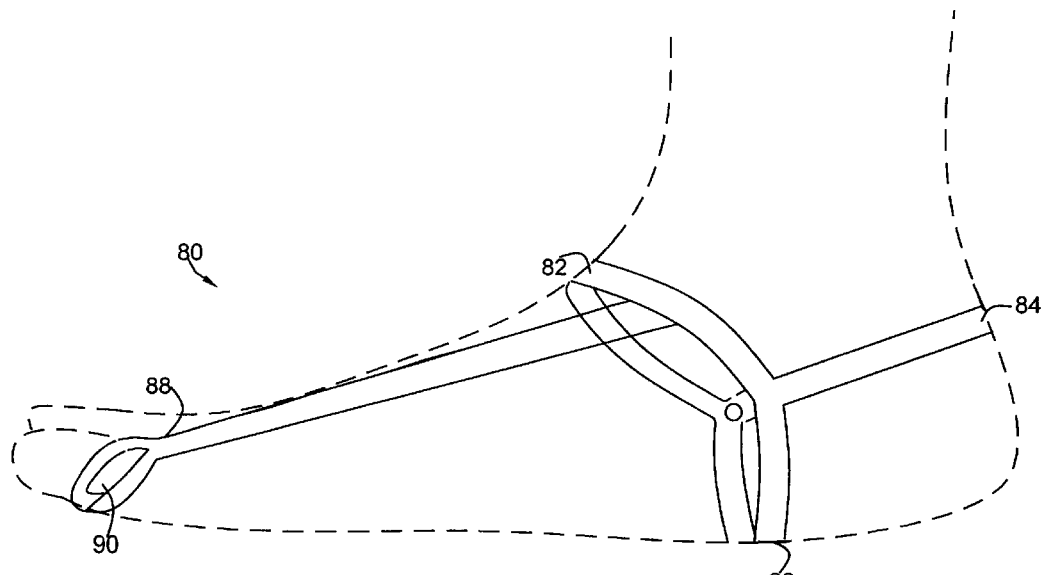
FIG. 7 is a perspective view of an alternative embodiment of the invention incorporating a band having a toe loop.
Figure 8:
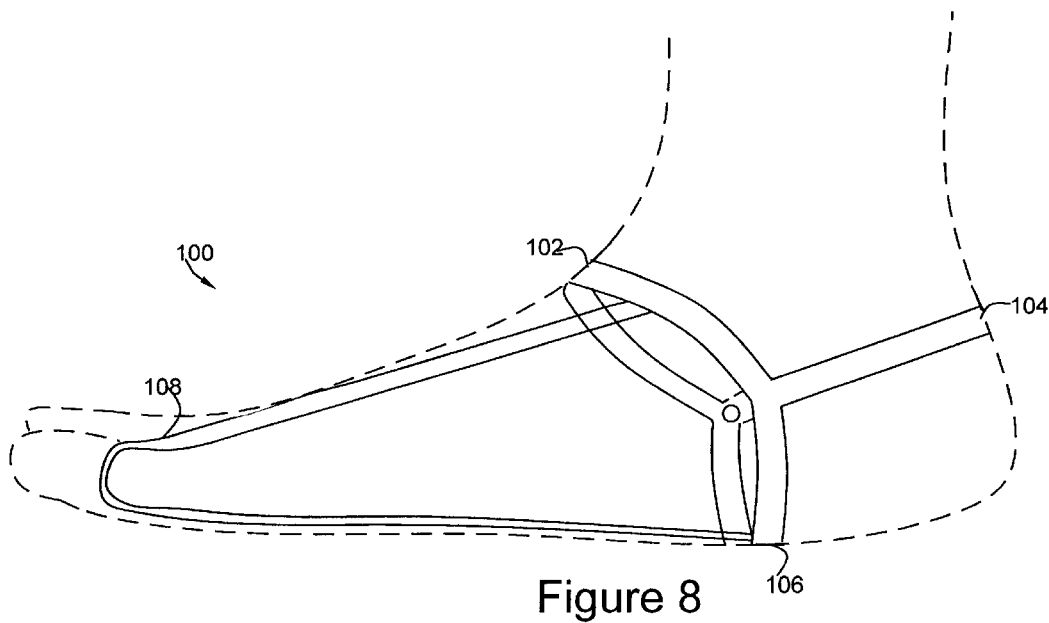
FIG. 8 is a perspective view of an additional embodiment of the invention having a band extending over and under the foot.

In an alternate embodiment, the toe loop band 80 of FIG. 7 uses the same basic configuration of front strap 82, back strap 84 and heel strap 86, with the addition of a toe strap 88. The toe strap 88 is generally narrower than the harness straps and is affixed to about the center of the front strap 82 and extends down to the big toe where the loop 90 harnesses the big toe. The loop 90 can be stitched into the toe strap 88 or can be affixed with Velcro®. Likewise, the toe strap 88 can be either stitched to the front strap 82 or removably affixed, and therefore movable along the front strap 82, as known in the art. Pressure devices are to be adhered to the loop 90 around the big toe to alleviate headaches; stimulate the thyroid, parathyroid, esophagus, vocal cords, pituitary gland, eyes, throat, neck, cervical spine, tonsils; and lymph glands. The pressure devices adhered to the loop 90 can be in addition to or separate from the pressure devices identified heretofore.

In another embodiment, the front strap 102, back strap 104 and heel strap 106 anchor a foot strap 108 that extended from the front strap 102, down over the foot, between the big toe and second toe, and is affixed to the heel strap 106. In the preferred embodiment, the foot strap 108 is movable along the front strap 102, heel strap 106 and/or back strap 104. The foot strap 108 enables the placement of pressure devices along the bottom portion of the foot strap 108, from the toes back to the heel. The ability to move the foot strap 108 across the width of the foot provides access to additional points. Along this path the following additional points are stimulated lungs, heart, kidney, liver, gallbladder, spleen, small intestine, colon, pancreas, bladder, thymus gland, solar plexus, adrenal glands, doudenum, diaphragm, ureter tubes, pyloris, and appendix. As described heretofore, the foot strap 108 can be removably or permanently affixed to the front strap 102 and heel strap 106.

Alternatively, the harness can be molded in one piece from a pliable plastic with the pressure devices either molded in or hot glued to the harness. In most embodiments, the preferred pressure device is a half round to maintain a smooth outer surface. Although reference is made herein to pearls, beads, etc., the pressure devices are not required to have a circular configuration, and other polygons can be used.

The disclosed band can also be used in conjunction with magnetic therapy. The pressure devices can be replaced with magnets and positioned in the appropriate position(s) along the disclosed device.

What is claimed is:

1. A foot harness to deliver pressure to reflex points on a user's foot and ankle, said band having:

a flexible front band, said front band having a first end and a second end;

a flexible rear band; said rear band having a first end and a second end, said rear band first end being affixed to said front band first end to form a first juncture and said rear band second end being affixed to said front band second end to form a second juncture;

a flexible heel band, said heel band having a first end and a second end, said heel band first end being affixed to said first juncture and said heel band second end being affixed to said second juncture;

at least one rigid pressure device, said at least one pressure device being positioned on said foot harness to lie in a relative unmoving position adjacent said user's skin, said foot harness being dimensioned to position each of said at least one pressure device at the center of an identified reflexology pressure point to apply pressure to said pressure point thereby directly affecting a corresponding remote portion of said user's body.

2. The foot harness of claim 1 wherein said front band first end, said rear band first end and said heel band are permanently affixed at said first juncture.

3. The foot harness of claim 1 wherein said front band first end, said rear band first end and said heel band are integral with one another to form said first juncture.

4. The foot harness of claim 1 wherein said rear band second end and said heel band second end are permanently affixed to one another at said second juncture.

5. The foot band of claim 4 wherein said front band second end is removably affixed to said second juncture.

6. The foot harness of claim 5 wherein said second juncture further contains a first part of a two part securing means and said front band second end contains a second part of a two part securing means.

7. The foot harness of claim 6 wherein said securing means enables the length of said front band to be adjusted.

8. The foot harness of claim 1 wherein a first pressure device is affixed to said first juncture and a second pressure device is affixed to said second juncture, said first and said second pressure device being positioned to be in contact with said user's skin.

9. The foot harness of claim 1 wherein at least one of said front band, said heel band and said rear band is a stretchable material.

10. The foot harness of claim 1 wherein said pressure devices are stitched to said foot band.

11. The foot harness of claim 1 wherein said pressure devices are polygons.

12. The foot harness of claim 11 wherein said polygons are spheres.

13. The foot harness of claim 11 wherein said pressure devices are semi-spherical, the curved portion of said semi-sphere being adjacent to said user's skin.

14. The foot harness of claim 1 further comprising a toe strap, said toe strap having a first end and a second end, said first end being affixed to said front band and said second end having a loop to slide over said user's toe.

15. The foot harness of claim 1 further comprising a foot strap, said foot strap having a first end and a second end, said first end being affixed to said front band and said second end being affixed to said heel band.

16. The foot harness of claim 15 wherein said foot strap is movable along said front band and said heel band thereby enabling said foot strap to be positioned along the user's foot.

17. The foot harness of claim 1 further comprising a Y-shaped, securing insert, said securing insert having affixing means at each end and dimensioned to receive said front band second end, said rear band second end, and said heel band second end, thereby forming said second juncture.

18. The foot harness of claim 17 wherein said second pressure device is affixed to the center of said Y shaped securing insert.

19. The foot harness of claim 1 wherein the length of said front band, said rear band and said heel band determine the placement of said pressure devices relative to the user's foot.

20. The foot band of claim 1 wherein said pressure devices are magnets.

21. A reflexology foot harness to deliver reflexology pressure to predetermined reflexology points on a user's foot and ankle, said band having:
    a flexible front band, said front band having a first end and a second end;
    a flexible rear band; said rear band having a first end and a second end, said rear band first end being permanently affixed to said front band first end to form a first juncture and said rear band second end being permanently affixed to said front band second end to form a second juncture;
    a flexible heel band, said heel band having a first end and a second end, said heel band first end being permanently affixed to said first juncture and said heel band second end being permanently affixed to said second juncture;
    affixing means, said affixing means being at said front band second end and said second juncture,
    at least one rigid pressure device, a first of said at least one pressure device being affixed to said first juncture and positioned to lie adjacent said user's skin and a second of said at least one pressure device being affixed to said second juncture and positioned to lie adjacent said user's skin.

22. The method of applying consistent pressure to reflexology points on a user's foot and ankle using a flexible foot harness having a front band, said front band having a first end and a second end; a rear band; said rear band having a first end and a second end, said rear band first end being permanently affixed to said front band first end to form a first juncture and said rear band second end being permanently affixed to said front band second end to form a second juncture; a heel band, said heel band having a first end and a second end, said heel band first end being permanently affixed to said first juncture and said heel band second end being permanently affixed to said second juncture; affixing means, said affixing means being at said front band second end and said second juncture, at least one rigid pressure device, a first of said at least one pressure device being affixed to said first juncture and positioned to lie adjacent said user's skin and a second of said at least one pressure device being affixed to said second juncture and positioned to lie adjacent said user's skin;
    comprising the steps of:
        a. locating the applicable pressure points on a user's foot and ankle;
        b. determining the appropriate size foot harness for the user;
        c. placing the foot harness on the user's foot;
        d. positioning the heel band under the user's foot and the rear band above the user's heel;
        e. positioning the each of said pressure devices adjacent said pressure points;
        f. securing said front band to said second juncture to maintain said foot harness on the user's foot; thereby causing said pressure devices to apply reflexology pressure to said applicable pressure points.

\* \* \* \* \*